(12) United States Patent
Moriyama et al.

(10) Patent No.: US 8,682,463 B2
(45) Date of Patent: Mar. 25, 2014

(54) DENTURE GRINDING MACHINE

(75) Inventors: Takeshi Moriyama, Kyoto (JP); Yusei Kadobayashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 382 days.

(21) Appl. No.: 13/168,044

(22) Filed: Jun. 24, 2011

(65) Prior Publication Data

US 2011/0318703 A1    Dec. 29, 2011

(30) Foreign Application Priority Data

Jun. 25, 2010 (JP) ................................. 2010-145274

(51) Int. Cl.
*G06F 19/00* (2011.01)

(52) U.S. Cl.
USPC ................. 700/97; 700/164; 433/68; 433/69; 433/70

(58) Field of Classification Search
USPC ............................ 700/97, 164; 433/68, 69, 70
See application file for complete search history.

(56) References Cited

U.S. PATENT DOCUMENTS

| | | | | |
|---|---|---|---|---|
| 2,106,125 | A * | 1/1938 | Roebuck et al. | 433/52 |
| 2,258,473 | A * | 10/1941 | Scott | 433/52 |
| 3,049,804 | A * | 8/1962 | Skinner | 433/29 |
| 6,568,936 | B2 * | 5/2003 | MacDougald et al. | 433/223 |
| 6,832,877 | B2 * | 12/2004 | Hamada | 409/96 |
| 8,423,166 | B2 * | 4/2013 | Moriyama et al. | 700/97 |
| 2002/0137002 | A1 | 9/2002 | Bodenmiller | |
| 2008/0311537 | A1 | 12/2008 | Minagi et al. | |
| 2011/0318703 | A1 * | 12/2011 | Moriyama et al. | 433/69 |
| 2011/0318709 | A1 * | 12/2011 | Moriyama et al. | 433/191 |

FOREIGN PATENT DOCUMENTS

| | | |
|---|---|---|
| EP | 1 245 332 | 10/2002 |
| JP | 61-45749 | 3/1986 |
| JP | 2005-253756 | 9/2005 |
| WO | 2009/035142 | 3/2009 |

OTHER PUBLICATIONS

Extended European Search Report (in English language) issued Aug. 24, 2012 in corresponding European Patent Application No. 11 00 5213.

* cited by examiner

*Primary Examiner* — Michael D Masinick
(74) *Attorney, Agent, or Firm* — Wenderoth, Lind & Ponack, L.L.P.

(57) ABSTRACT

A denture grinding machine includes: a denture-holding table for holding dentures; a grinding tool for grinding the dentures held on the denture-holding table; a main body for holding the grinding tool; a moving mechanism for causing relative movement between the denture-holding table and the main body; and a driving mechanism for relatively driving the main body and the denture-holding table. The moving mechanism moves relatively the denture-holding table and the main body in three-dimensional coordinate directions based on grinding portion data, and the grinding tool performs grinding of the denture occlusal surface from a direction perpendicular to the occlusal surface.

12 Claims, 8 Drawing Sheets

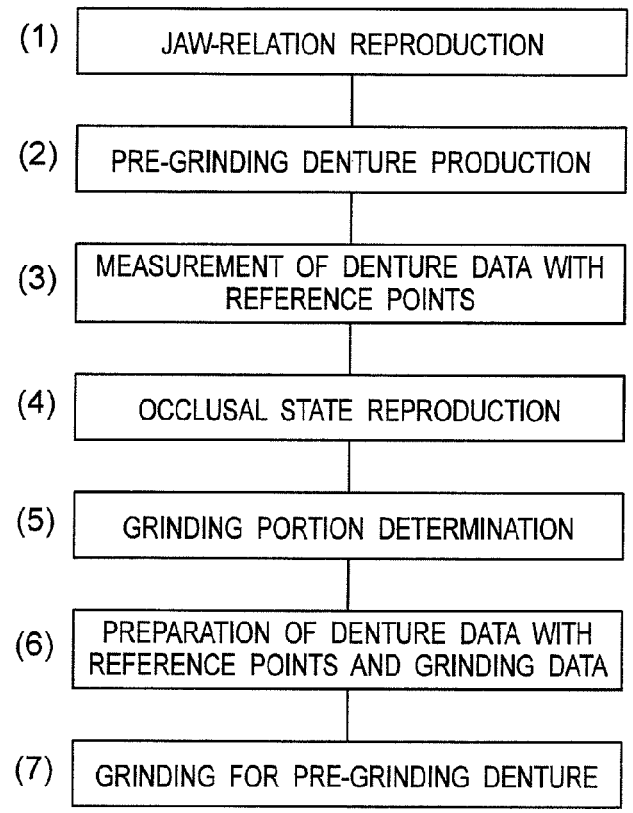
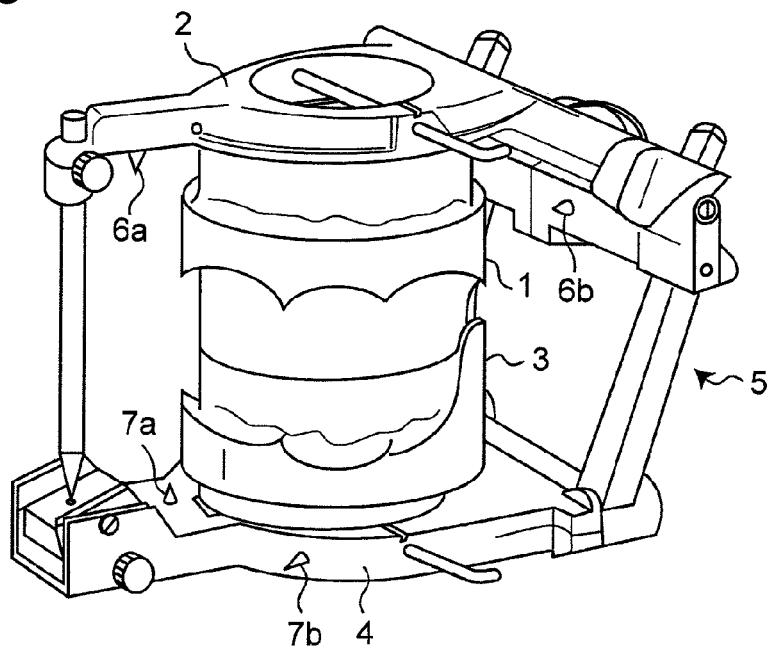

Fig.7
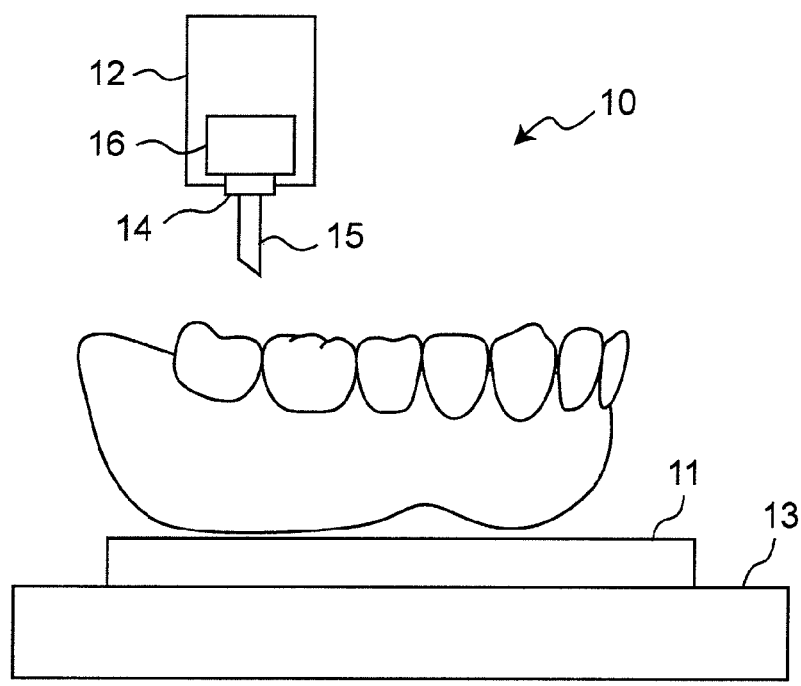
Fig.8
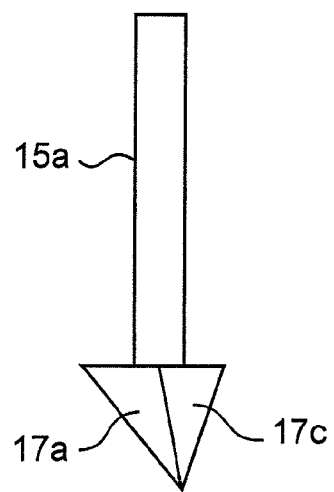
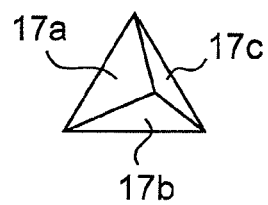

DENTURE GRINDING MACHINE

BACKGROUND OF THE INVENTION (1) Field of the Invention

The present invention relates to a denture grinding machine for grinding an occlusal surface of dentures.

(2) Description of Related Art

Conventionally, grinding of an occlusal surface of dentures has been performed manually using a polishing instrument. For this reason, long experience and knowledge of occlusion have been required for dentists. Considerable skills have been required for grinding works suitable for occlusion movements of patients.

In JP-A-61-45749, an automatic grinding machine for artificial teeth is described. In this grinding machine, a maxillary denture is held in the maxillary frame of an articulator and a mandibular denture is held in a mandibular frame, and the maxillary frame is moved reciprocately at least in a horizontal direction.

However, the grinding machine of JP-A-61-45749 only makes the maxillary frame move reciprocately while keeping the maxillary denture and the mandibular denture in direct contact with each other. Since reciprocating movement does not suit to the occlusion movement of a patient, a correct occlusion-state has not been obtained. In addition, the maxillary denture and the mandibular denture are slide contacted with each other to generate a large noise. Thus, the use of such a machine in a dental clinic has been obstacles to clinical treatment.

Prior Art Document
JP-A-61-45749

SUMMARY OF THE INVENTION

An object of the present invention is to provide a denture grinding machine which can perform grinding suitable for an occlusion movement of a patient with a little noise.

In order to achieve the above object, a first aspect of the present invention provides a denture grinding machine including:

a denture-holding table for holding dentures;

a grinding tool for grinding the dentures held on the denture-holding table;

a main body for holding the grinding tool;

a moving mechanism for causing relative movement between the denture-holding table and the main body; and a driving mechanism for relatively driving the main body and the denture-holding table, wherein the moving mechanism moves relatively the denture-holding table and the main body in three-dimensional coordinate directions based on grinding portion data, and the grinding tool performs grinding of the denture occlusal surface from a direction perpendicular to the occlusal surface.

Preferably, the grinding tool has a grinding surface on a tip thereof inclined with respect to an axis line, where the polishing surface faces at least one of an occlusion facet on a moving side, an occlusion facet of a working side, and an occlusion facet at forward moving, of the artificial tooth that forms the denture.

Preferably, the drive mechanism is a vibratory device with an ultrasonic vibrator.

The grinding portion data to be used is prepared by:

(1) a jaw-relation reproduction step of determining a jaw-relation reproduction condition by measuring a jaw movement of a patient, and reproducing a jaw state of the patient on an occlusion-state reproducing apparatus in accordance with the jaw-relation reproduction condition;

(2) a pre-grinding denture production step of arranging dentures on the occlusion-state reproducing apparatus in accordance with the jaw-relation reproduction condition and preparing pre-grinding dentures;

(3) a measurement step for denture data with reference points of measuring denture data with reference points which is three-dimensional image data containing reference points that represents a positional relationship between the jaw-relation reproduction condition and the dentures and an occlusal surface of the dentures;

(4) an occlusion-state reproduction step of reproducing an occlusion state of the denture data with reference points by using the jaw-relation reproduction condition on a three-dimensional image;

(5) a grinding data determination step of determining grinding data of grinding portions under a dynamic condition or set condition from a portion surrounded by an image of upper and lower jaws on the three dimensional image in a reproduced occlusal state; and (6) a preparation step for denture data with reference points having grinding data for preparing denture data with reference points having grinding data, where the denture data with reference points is additionally provided with the grinding data.

According to the first aspect of the present invention, compared with the conventional manual labor, grinding can be performed quickly and correctly.

During treatment time, polishing work can be performed and completed. Maxillomandibular conformity is good.

Since polishing is performed without applying a burden to dentures, the dentures can be prevented from being damaged.

The sharp portion of a cutting piece can be deminished.

Amount of polishing can be changed by changing the kind of oscillation.

It is suitable for cutting and polishing the surface of a small portion as in an occlusal adjustment or the like.

The use of a moving mechanism capable of not only linearly moving in X, Y, and Z axial directions but also rotationally moving in X, Y, and Z axial directions may lead to more precise production of dentures.

According to the second aspect of the present invention, since a tip portion is suitable in a cutting direction, there is a little movement of the denture-holding table. Thus, a cutting time can be reduced. Since a jig of the same angle is used, a polishing surface can be made uniform.

According to the third aspect of the present invention, polishing can be performed quietly and stably. Thus, the denture grinding machine can be placed in a dental clinic or the like.

According to the fourth aspect of the present invention, dentures are reproduced from an occlusion-state of denture data to a three-dimensional image, and grinding data defined from a portion surrounded by a maxillomandibular image is used. Thus, maxillomandibular conformity and maxillomandibular accessibility are improved.

BRIEF DESCRIPTION OF THE DRAWINGS

FIG. 1 is a flowchart illustrating a denture-grinding method according to the present invention;

FIG. 2 is a perspective diagram illustrating a state where a maxillomandibular model is attached to an articulator having reference points;

FIG. 7 is a schematic diagram illustrating the configuration of a denture grinding machine;

FIG. 8 is a diagram illustrating a front view of a grinding tool and a view from the tip of a processing section according to a first embodiment;

DETAILED DESCRIPTION OF PREFERRED EMBODIMENTS

Figure 3:
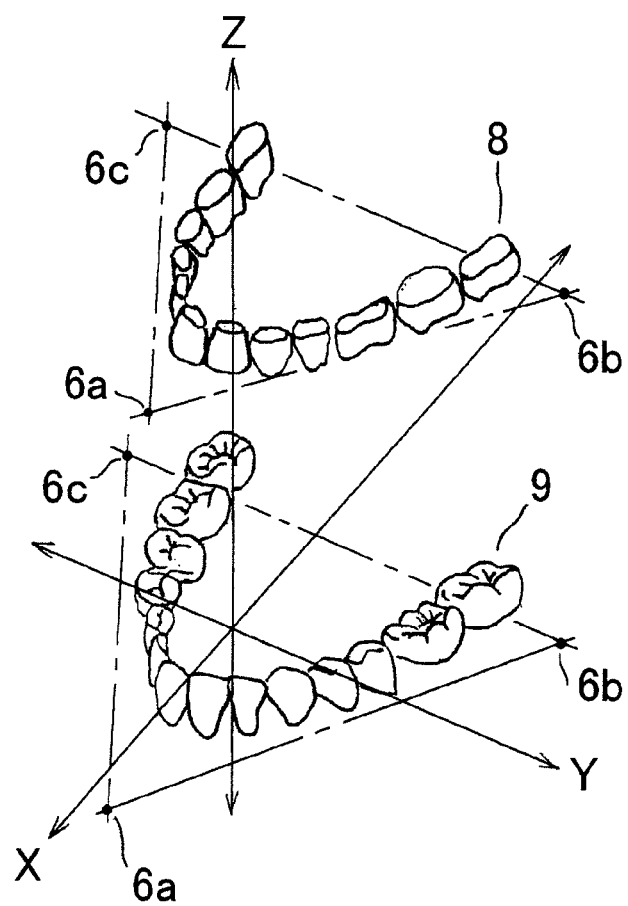
FIG. 3 is a diagram representing three-dimensional data of maxillomandibular occlusal surfaces on a three-dimensional space.

Hereinafter, embodiments of the present invention will be described with reference to the accompanying drawings.

A typical process for producing a denture is as follows:

1. An intraoral form of a patient is taken to prepare an impression.

2. An intraoral model of the patient is made of plaster using the impression and a constituent resin base plate is prepared on the model.

3. Wax is poured into a mold form and fixed in the shape of an arch. The wax is then mounted on the base plate to form a wax rim on which artificial tooth are arranged. A combination of this wax rim and the base plate is referred to as a bite plate.

4. The bite plate is applied to a patient to take a bite form of the patient.

5. Maxillary and mandibular models equipped with the bite plate is attached to an articulator to reproduce an occlusion state on the articulator.

6. Artificial tooth suitable for the patient are selected and maxillary anterior artificial teeth are arranged first on the maxillary wax rim and then mandibular anterior artificial teeth on the mandibular wax rim.

7. The maxillary height is slightly increased by adjusting an incisal pole of the articulator and mandible and maxillary molar artificial teeth are then arranged on the wax rim.

8. The incisal pole of the articulator is returned to the original state and an occlusal adjustment for grinding high portions is performed. In the occlusal adjustment, an articulating paper is sandwiched between the upper jaw and the lower jaw and a portion that strongly comes into contact with the opposite portion is ground.

9. A cervix (neck portion) state and a gingival regional state of the anterior teeth are reproduced.

10. The denture model with artificial teeth arranged on the bite plate is applied to the buccal cavity of the patient on a trial basis and information about required correction is then obtained.

11. Portions which should be corrected are corrected according to the information.

12. The denture model is separated in a flask (frame) and embedded in plaster and solidified.

13. The flask is heated to soften the wax of the denture model and the flask is removed to melt the wax, resulting in a mold.

14. A separation material is applied to the plaster portion of the mold and resin for denture plate (synthetic resin)) is then poured into the mold. The upper and lower mold forms are combined together and then pressed by a press.

15. Excessive resin is removed and the upper and lower frames are set, followed by being subjected to heat to harden the resin.

16. The mold forms are removed and the plaster is then taken out to scrape out the denture.

17. The denture is attached to the articulator again and occlusal imbalance caused by contraction occurred in resin hardening is then corrected. Articulating paper is used in occlusal correction.

18. Occlusion when the jaw is moved back and forth and left and right is adjusted with an articulating paper (this adjustment is a last occlusal adjustment and called grinding).

19. Removing burrs from the resin, polishing is performed.

In the step of producing a denture, the intraoral form is taken, the wax rim is formed, the artificial teeth are arranged, and the wax is replaced with the resin by a lost-wax process. In this case, the contraction of the resin causes a positional displacement of artificial teeth and interference occurs when the artificial teeth are bitten as dentures by the upper and lower jaws. The grinding is the adjustment of such an interference portion. Even if the occlusion is correctly performed on the dentures, the grinding may be performed to change the occlusal relationship depending on the status of the buccal cavity of the patient. The adjustment is performed in corporation with the movement of the jaws of the patient. According to the present invention, a series of these operations is performed using a program.

Here, in the case of a denture-grinding method, full dentures are preferable. Alternatively, partial dentures may be also used even in the case where the upper and lower jaws are a combination of dentures.

1. Denture Grinding Method

The denture-grinding method of the present invention includes the following processes as illustrated in FIG. 1.

(1) Jaw-relation reproduction step (2) Pre-grinding denture production step (3) Measurement step for denture data with reference points (4) Occlusal state reproduction step (5) Grinding portion determination step (6) Preparation step for denture data with reference points having grinding data (7) Grinding step for pre-grinding dentures (1) The jaw-relation reproduction step in which the jaw-relation reproduction conditions that can reproduce the conditions of the jaws of the patient are determined to reproduce the jaw relation will be described.

The jaw-relation reproduction step reproduces a positional relationship between the upper and lower jaws of the patient before the production of dentures. Usually, by using an articulator, the maxillomandibular movement is reproduced on the articulator by adjusting the movement of the condyle path of the articulator and incisal movement in corporation with the movement of the jaws.

It is necessary to decide moving directions that assume masticatory motion and opening/closing movement from the maxillomandibular centric occlusal position.

The conditions of the jaws of the patient include static conditions and dynamic conditions. Typically, the conditions include the position of the centric occlusal position and the directions of protrusive movement and lateral movement, and sometimes the direction of hinge movement.

These occlusal conditions can be reproduced by an occlusion-state reproducing apparatus, typically an articulator. The articulator can reproduce static relations and dynamic relations exactly.

The jaw-relation reproduction conditions include a sagittal condylar inclination, a balancing-side lateral condyle path, a regulatory mechanism of immediate side-shift, and a regulatory mechanism for an angle of lateral condyle path on the working side. Examples of the incisal path regulatory mechanism include a sagittal incisal path inclination and a lateral incisal path guide angle.

The method using the approximate values of the jaw movement in connection with the conditions of the patient is common. For example, the standard condylar distance is 110 mm, the distance between upper and lower arch is 110 mm, the maximum mandibular movement angle is 120 degrees, the inclination of sagittal condylar path is 30 degrees, and the angle of lateral condyle path is 15 degrees.

An important point is that it becomes clear how the upper jaw moves with respect to the lower jaw when the lower jaw is shifted from the centric occlusal position to the lateral movement.

As the simplest method, it is also possible to set the jaws so that the upper jaw slides forward at an angle of 10 degrees from the centric position in parallel to the lower jaw and the upper jaw further slides in the upper direction at an angle of 20 decrees with respect to the occlusal surface from the centric occlusal position.

In recent years, a method for directly reproducing a jaw movement has been investigated and a jaw-movement measurement apparatus has been developed. The jaw movement may be directly acquired by a jaw-movement measurement apparatus so that the jaw movement may be reproduced by a jaw-movement reproducing apparatus.

(2) The pre-grinding denture production step of producing a pre-grinding denture will be described. Here, dentures are produced according to the jaw-relation reproduction conditions of the occlusion-state reproducing apparatus to produce pre-grinding dentures before the step of grinding.

The pre-grinding denture production step is a step of producing dentures according to the maxillomandibular relation obtained in the above occlusion-state reproduction step. In other words, the pre-grinding denture production step is a step of producing a normal denture (steps 6 and 7 in the above denture production process). In the typical process, a wax rim is formed, artificial teeth are arranged along the wax rim and a pre-grinding denture is prepared by a lost wax process. Here, the production method is not particularly limited but the pre-grinding denture can be produced by any typical procedure.

The pre-grinding denture is not ground, so that it cannot be correctly occluded on the occlusion-state reproducing apparatus yet. In order to carry out correct occlusion on the occlusion-state reproducing apparatus, the grinding of the occlusal surface is performed according to the present invention.

(3) The step for measuring denture data with reference points by a denture data measurement apparatus will be described. Here, the denture data measurement apparatus measures the denture data with reference points, comprising three-dimensional image data of the occlusal surface of the denture and reference points representing a positional relation between the occlusion-state reproducing apparatus and the denture.

In this step, the position of the pre-grinding denture in the occlusion-state reproducing apparatus is measured so that an occlusion state can be reproduced in a computer in addition to obtaining the 3D-data of the produced pre-grinding denture. By setting up the maxillomandibular relation of the occlusion-state reproducing apparatus in advance, the occlusion state can be reproduced.

At least three reference points are required for the respective upper and lower arches of the reproducing device. Alternatively, three sides may be used. One side and one point are preferable. Specifically, it may be configured of three needle-like form or spherical surface (preferably globular shape) or may be a combination of a straight side and spherical surface of the reproducing device. Here, the 3D-data is necessary to have reference points for correctly calculating the maxillomandibular relation to be reproduced on a computer. A spherical surface is preferable in order to match the 3D-data on a computer.

The occlusion-state reproducing apparatus that determines the jaw-relation reproduction condition used for a denture grinding method is an articulator 5 having an upper arch 2 on which an upper jaw model 1 is attached and a lower arch 4 on which a lower jaw model 3 is attached. Preferably, as illustrated in FIG. 2, reference points 6a, 6b, and 6c and reference points 7a, 7b, and 7c are provided on the upper arch 2 and the lower arch 4, respectively.

(4) The occlusion-state reproduction step, which reproduces the occlusion state of the denture data with reference points by using the jaw-relation reproduction conditions, will be described.

In this step, an occlusion state is reproduced on a computer. The maxillomandibular relation of the occlusion-state reproducing apparatus can be arbitrarily configured on the computer.

Here, the positional relationship between the upper and lower jaws can be correctly simulated in the space of the computer. In the computer, the static relationship between the upper jaw and the lower jaw is represented. This relationship includes the reference points which are used for acquiring 3D-data. In the space of the computer, the movements of upper and lower jaws are simulated so that the 3D-data of the upper and lower jaws represents a static relation.

Preferably, the mandibular orthogonal coordinate system of the lower jaw and the orthogonal coordinate system of the upper jaw are configured. To reproduce the maxillomandibular occlusal state, from an arbitrary positional relationship between the upper and lower jaws, a direction along which the orthogonal coordinate system of the upper jaw moves with respect to the orthogonal coordinate system of the lower jaw may be arbitrarily calculated.

As illustrated in FIG. 3, the reference points on the orthogonal coordinate system of the lower jaw and the reference points on the orthogonal coordinate system of the upper jaw are preferably coincided with the reference points on the computer to reproduce the relationship between the movement of the denture data 8 of the upper jaw and the denture data 9 of the lower jaw.

In each orthogonal coordinate system, the positions of reference points are defined and aligned with the denture data obtained in the step of measuring the denture data.

Figure 4:
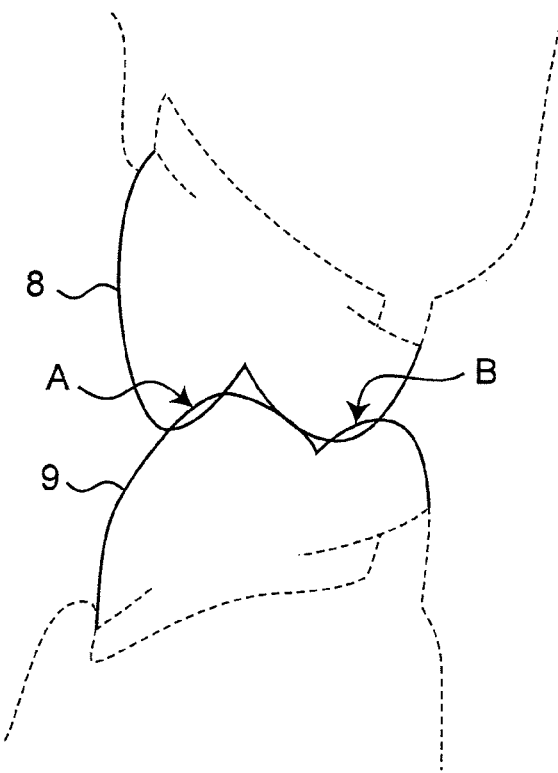
FIG. 4 is a diagram illustrating an occlusion state of the three-dimensional data of the axillomandibular occlusal surfaces.

As shown in FIG. 4, it can also set up so that an upper jaw orthogonal coordinate system may move to a lower jaw orthogonal coordinate system so that each coordinate axis performs the movement of the denture data 8 of the mandibular denture data 9 represented in the occlusion-state reproduction step.

(5) The determination step for grinding portion, which determines grinding data under static conditions or defined conditions from a portion surrounded by the image of upper and lower jaws from the reproduced occlusion state, will be described.

Here, the region surrounded by the 3D data set in the step of reproducing the occlusion state, that is, as shown in FIG. 4, the region where the occlusion surface of the artificial tooth of the upper jaw and the occlusion surface of the artificial tooth of the lower jaw are overlapped, is observed.

In the case where the region surrounded by the 3D-data is small, the dentures lack in stability. Thus, an overlapped portion of maxillomandibular 3D-data is adjusted by the hinge movement of maxillary 3D-data or movement thereof in the direction of lowering an occlusal vertical dimension. If the overlapped portion of the 3D-data is large, there is no cusp of the tooth due to a large number of cuttings. Thus, an overlapped portion of maxillomandibular 3D-data is adjusted by the hinge movement of maxillary 3D-data or movement thereof in the direction of increasing the occlusal vertical dimension. The hinge movement or the shift in occlusal vertical dimension may be used in arbitrarily combination.

Figure 5A:
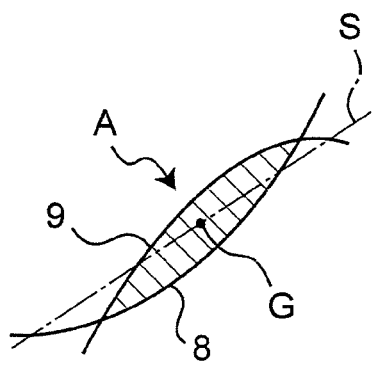
FIG. 5A is a diagram illustrating a portion surrounded by the three-dimensional data of the maxillomandibular occlusal surfaces.

Next, as illustrated in FIG. 5A, a grinding surface is determined by moving the maxillary 3D-data 8 or the mandibular 3D-data 9 so that the 3D-data overlapped portion A is frictionally moved during the movement of the upper and lower jaws. It is performed by cutting each 3D-data overlapped portion along the arbitrary defined grinding surface S at the time of forward movement, back movement, or lateral movement from the centric occlusal position.

Figure 5B:
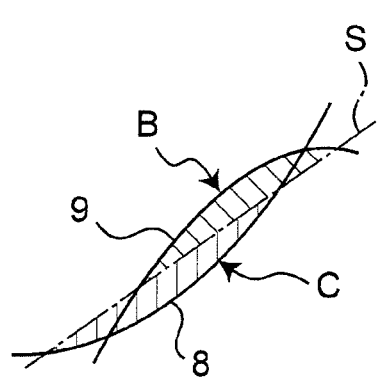
FIG. 5B is a diagram illustrating a grinding portion of the maxillomandibular occlusal surfaces.

Although the grinding surface S may not pass through the maxillomandibular 3D-data overlapped portion, preferably, it may pass through the overlapped portion between the maxillary 3D-data 8 and the mandibular 3D-data 9. As illustrated in FIG. 5B, cuspal portions B and C surrounded by the surface extended from the grinding surface S in the overlapped portion between 3D-data 8 and 9 are provided as cutting portions, respectively. These portions are referred to as grinding portions and the data thereof is referred to as grinding data.

The arbitrary defined grinding surface S is a surface extending in the direction of a forward movement, a backward movement, or a lateral movement and the angle of each surface is arbitrary defined with respect to an occlusal plane. It is preferable that the angle of the grinding surface S is set to 5 to 60 degrees with respect to the occlusal plane. An angle of a surface where the cusp of tooth touches is preferably 5 to 45 degrees in the forward or backward direction and 20 to 60 degrees in the lateral movement.

The movement direction is a direction along which the maxillary orthogonal coordinate system moves with respect to the mandibular orthogonal coordinate system at an arbitrary point within the range surrounded by the maxillary 3D-data and the mandibular 3D-data in the dynamic relation represented by the occlusion-state reproduction step. The movement direction is preferably linear. Alternatively, the movement direction may be curved. The movement direction may be approximate to a straight line. Alternatively, a curved line may be applied to the movement direction. In other words, the movement direction is a straight line or a curved surface. Preferably, it is a straight line or cylindrical surface.

Furthermore, the arbitrary point in range A surrounded by the maxillary 3D-data 8 and mandibular 3D-data 9 is the center of gravity G of the range surrounded by maxillary 3D-data 8 and the mandibular 3D-data 9.

When the range surrounded by the maxillary 3D-data 8 and the mandibular 3D-data 9 is represented by n points on the space, the center of gravity G is preferably calculated as X', Y', Z' obtained by converting X, Y, and Z axis of a mandibular orthogonal coordinate system and X, Y, and Z axis of a maxillary orthogonal coordinate system XYZ axis into those of the same orthogonal coordinate system, respectively, and dividing the sums of the values of the respective axes X, Y, and Z are divided by n. The grinding surface S is a plane including the movement direction of the upper jaw with respect to the lower jaw that passes through the values of X', Y', and Z'.

This movement direction is calculated by the reproduction method represented in the occlusion-state reproduction step. When the movement direction is reproduced by the articulator, these adjustment mechanisms can be reproduced on the computer in the case of an arcon type articulator or a condylar type articulator. The arcon type articulator is preferable.

The condylar distance of the articulator is 50 to 170 mm, preferably 80 to 140 mm, more preferably 100 to 120 mm. It is preferred to have an average condylar distance as a fixed value of 110 mm. A distance between the upper arch and the lower arch is about 80 to 120 mm. Any distance between the upper arch and the lower arch is allowable as long as it is determined where appropriate.

The condylar distance and the distance between the upper arch and the lower arch are calculated from numerical values previously defined by the condyle path regulatory mechanism and the incisal patch regulatory mechanism, which specify the maxillomandibular movement of the articulator.

Specifically, examples of the condyle path regulatory mechanism include an inclination of sagittal condylar path, a balancing-side lateral condyle path, a regulatory mechanism for immediate side-shift, and a regulatory mechanism for an angle of lateral condyle path on the working side. Examples of the incisal path regulatory mechanism include a sagittal incisal path inclination and a lateral incisal path guide angle.

An inclination of sagittal condylar path is −30 degrees to +90 degrees, preferably −0 degree to +50 degrees, more preferably −20 degrees to +80 degrees.

A balancing-side lateral condyle path is 0 degrees to +40 degrees, preferably +10 degrees to +20 degrees, more preferably 0 degree to +30 degrees.

A regulatory mechanism for immediate side-shift is 0 to 5 mm, preferably 0 to 8 mm, more preferably 0 to 10 mm.

A regulatory mechanism for an angle of lateral condyle path on the working side is −50 degrees to +60 degrees, preferably −40 degrees to +50 degrees, more preferably −30 degrees to +30 degrees.

A sagittal incisal path inclination is −30 degrees to +90 degrees, preferably −20 degrees to +80 degrees, more preferably −10 degrees to +75 degrees.

A lateral incisal path guide angle is −0 degree to +90 degrees, preferably −0 degrees to +50 degrees.

The maxillary orthogonal coordinate system is calculated with respect to the mandibular orthogonal coordinate system, which can move in accordance with these regulation mechanisms.

From the names or the like of commercial articulators, settings which can appropriately select only adjustment items are preferable. In the case where an unadjustable articulator is used, it is preferable that the fixed values of the articulator are fixedly entered without change when the name of this articulator is selected. The defined conditions are conditions being set to remove protruded portions to prevent upper and lower jaws from being caught while allowing them smoothly rubbing with each other.

The grinding data obtained in the present step is used as CAD data for grinding dentures. An NC program for processing in the grinding step for pre-grinding dentures is prepared. A computer numerical control (CNC), which controls a moving distance, a moving speed, and so on of tools in machine work by a computer, is used for grinding dentures. This process is referred to as CAM.

Figure 6:
FIG. 6 is a diagram illustrating a grinding portion of the occlusal surface.

FIG. 6 is a diagram illustrating faces to be ground in occlusal surfaces. Grinding is performed substantially in a bilaterally-symmetric manner. Thus, lead lines 1, 2, and 3 represent only one of jaws, respectively. When the upper and lower jaws are occluded, occlusal facets, where the upper and lower jaws make contact with each other, come into surface contact with the corresponding ones. Thus, the occlusal facets become surfaces being rubbed in accordance with the movement of the jaws.

Lead line 1 denotes posterior occlusal facets, lead line 2 denotes protrusive occlusal facets, and lead line 3 denotes balancing occlusal facets.

In other words, in the figure, reference numeral 1 denotes each of the surface portions to be ground at a certain angle, 2 denotes each of the surface portions to be ground at another angle, and 3 denotes the surface portions to be ground at a still another angle. However, these surfaces represented by these reference numerals are illustrative only. When considering occlusal static or dynamic relation, it is preferable to adjust or calculate the angles of the respective surfaces so that the surfaces are rubbed with the corresponding surfaces in their correct directions. Alternatively, however, these surface portions may be those to be ground almost at the same angle.

(6) The preparation step for denture data with reference points having grinding data, in which the denture data with reference points having grinding data, where denture data with reference points is additionally provided with grinding data, is prepared, will be described.

The grinding surface, which is the above grinding data, is aligned with the denture data with reference points to determine a grinding portion, thereby obtaining denture data reference points having grinding data. Here, based on the reference points, an important point is that a portion which should not be ground and a portion which should be ground are defined based on the reference points.

Therefore, by overlapping the indication parts of the reference points that represents a positional relationship between dentures and the reference point portions of the denture data with reference points having grinding data together, grinding portions of the dentures can be determined.

(7) A grinding step for pre-grinding dentures, which grinds a pre-grinding denture based on the denture data with reference points having grinding data, will be described.

Grinding data is used as CAD data and create an NC program for processing in this step. This is a program of a computer numerical control (CNC) which controls a moving distance, a moving speed, and so on tools in machine work by a computer. Grinding of dentures is performed using this program.

FIG. 7 is a schematic diagram illustrating the configuration of a denture grinding machine according to the present invention. The denture grinding machine 10 includes a denture-holding table 11 and a grinding machine main body 12 provided above the denture-holding table 11.

The denture-holding table 11 has a denture-holding surface in an X-Y axial plane, and is configured to fix and hold a grinding-target denture, which is a target to be ground, on the denture-holding surface. The denture-holding table 11 is movable or rotatable with a flexibility of 6 (movements in X, Y, and Z axial directions and rotations around the respective axes) by a moving mechanism 13.

The grinding machine main body 12 has a chuck 14 to hold a grinding tool 15 in parallel with a Z axis perpendicular to an X-Y axial plane. The grinding machine main body 12 is provided with a vibratory device 16 as a driving mechanism. The vibratory device 16 includes an ultrasonic vibrator that drives the grinding tool 15 relative to the denture-holding table 11 in the Z axial direction. Based on grinding portion data, the oscillation of the grinding tool 15 by the vibratory device 16 allows the occlusal surface of a denture on the denture-holding table 11 to be polished in the direction perpendicular to the occlusal surface, thereby completing grinding.

The frequency of the grinding tool 15 by the vibratory device 16 is 10 kHz to 100 kHz, preferably 15 kHz to 30 kHz. The vibrating direction of the grinding tool 15 corresponds to the axial direction of the grinding tool 15, namely the Z axial direction. In addition to an ultrasonic wave oscillation, for improving grinding efficiency, it is preferable that the grinding tool 15 may be provided with circular movement or reciprocating movement in parallel with the grinding surface or an ultrasonic wave or vibration with a different frequency bandwidth.

In this embodiment, the moving mechanism 13 is mounted on the denture-holding table 11 and the driving mechanism 16 is mounted on the grinding machine main body 12. Alternatively, however, the moving mechanism 13 may be mounted on the grinding machine main body 12 and the driving mechanism 16 may be mounted on the denture-holding table 11.

A cross-sectional shape of the axis of the grinding tool 15 is preferably in the form of a D-shape, a triangle, or a square other than a circle to make the grinding tool 15 easily fix and position on the chunk 14.

Preferably, the tip of the grinding tool 15 has a surface out of parallel with the occlusal surface. This is because the slope of the cusp of the artificial tooth that forms a denture is formed by a balancing occlusal facet, posterior occlusal facet, and a protrusive occlusal facet. Generally, each artificial tooth has a constant balancing occlusal facet, posterior occlusal facet, and a protrusive occlusal facet. In this case, grinding of the same occlusal facets of the respective artificial teeth is performed at the same angle. Thus, the same grinding tool may be used. In addition, the balancing occlusal facet, posterior occlusal facet, and a protrusive occlusal facet of each artificial tooth are constant, a flexibility of 3 for rotation around X, Y, and Z axes is not required, while a flexibility of 3 for horizontal movement in X, Y, and Z axial directions is required.

Figure 9:
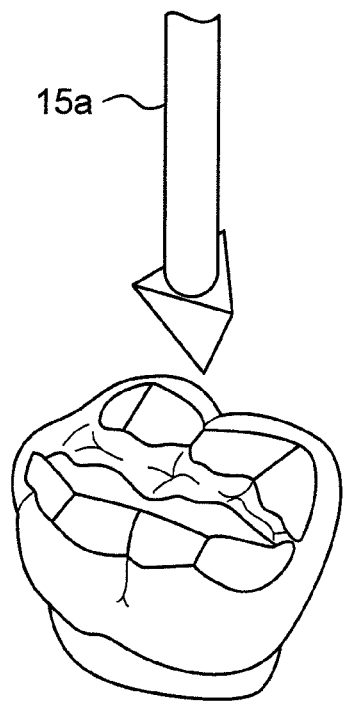
FIG. 9 is a perspective diagram illustrating a state of grinding an occlusal surface of a denture by the grinding tool of FIG. 8.

FIG. 8 illustrates a grinding tool 15a having processing surfaces, where an axis is provided with a circular cross-section and a tip is in the form of a triangular pyramid. As illustrated in FIG. 9, processing surfaces 17a, 17b, and 17c of the triangular pyramid are formed so that the grinding of a balancing occlusal facet, a posterior occlusion facet, and a protrusive occlusal facet can be performed. Four grinding tools 15a are sufficient for one pair of jaws, i.e., the maxillary left side, maxillary right side, mandibular left side, and mandibular right side.

Figure 10:
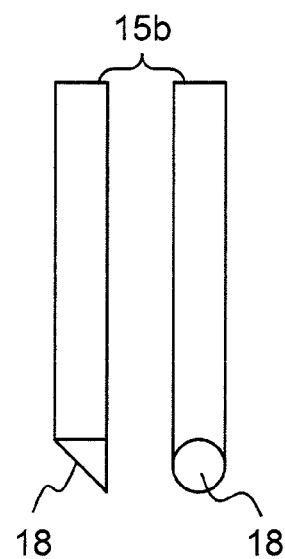
FIG. 10 is a diagram illustrating a front view and a side view of a grinding tool according to a second embodiment.

FIG. 10 illustrates a grinding tool 15b having a processing surface 18 which is inclined at a certain angle with respect to an axis having a circular cross-section.

Figure 11:
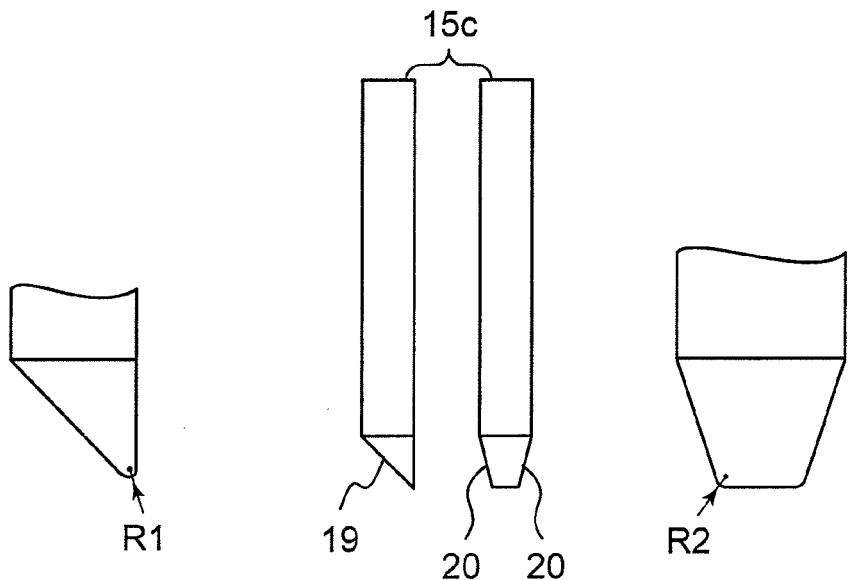
FIG. 11 is a diagram illustrating a front view of a grinding tool and an enlarged view of the processing section thereof, and a side view and an enlarged view of the processing section thereof according to a third embodiment.

FIG. 11 illustrates a grinding tool 15c having a processing surface 19 which is inclined at a certain angle with respect to an axis having a square-shaped cross-section, where the both side ends of the processing surface 19 form a tapered portion 20 so as to be narrowed toward the tip.

These grinding tools 15b and 15c should be independently provided for the balancing occlusal facet, posterior occlusal facet, and protrusive occlusal facet. Thus, 12 grinding tools in total are required for one set of jaws.

Figure 12:
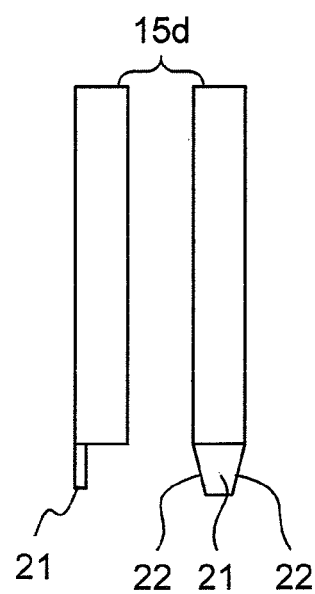
FIG. 12 is a diagram illustrating a front view and a side view of a grinding tool according to a fourth embodiment.

FIG. 12 illustrates a grinding tool 15d having a plate-shaped processing section 21 on an axis, which has a square-shaped cross section, and a tip. Both side ends of the processing section 21 form a tapered portion 22 so as to be narrowed toward the tip.

Except of the grinding tool 15b having the plate-shaped processing section 21 in FIG. 12, the angles of the respective processing surfaces 17a, 17b, 17c, 18, and 19 of the grinding tools 15a to 15c are set to 80 degrees or less to prevent the tips of the grinding tools 15a to 15c from touching the neighboring cusp. However, if the slope is steep, it may be easily broken. Thus, the angle is preferably in the range of 30 to 60 degrees, more preferably 40 to 60 degrees.

In the case of the grinding tools 15c and 15d in FIGS. 11 and 12, the widths of the processing surface 19 and processing section 21 is 1 to 6 mm, preferably 2 to 4 mm, more preferably 3 to 4 mm. If the widths of the processing surface 19 and the processing section 21 are wide, they may be brought into contact with other cusps. On the other hand, if their widths are narrowed, grinding should be repeated many times to grind a wide grinding surface, which affects working efficiency.

The materials of cutting materials for forming grinding tool 15 are not specifically limited, however, the materials may be a diamond-type, calcined-type (inorganic calcined products, such as alumina and zirconia), composite-types, and steel-types, and the like. Preferable materials are diamond-type and calcined-type.

As illustrated in FIG. 11, the roundness R1 of the tip and the roundness R2 of the both tip side ends of the grinding tool 15c (each represented by radius) is 0.5 to 0.05 mm, preferably 0.4 to 0.1 mm, more preferably 0.25 to 0.15 mm. If it is too thin, wear will occur. The tip roundness R1 and the both tip side-end roundness R2 of the grinding tool 15 do not need to be the same.

On the other hand, the width of a groove or cavity between the grinding surfaces on a denture to be ground by the grinding tool 15 is preferably 1.0 to 0.1 mm. If the width of the groove or cavity is insufficient, it is possible to reproduction. A valley between buccal cusps or between lingual cusps is preferably 0.8 to 0.2 mm. In order to perform delicate grinding, it is preferably 0.7 to 0.4 mm. If the formation of a groove or cavity during grinding is insufficient, it may be reformed using the tip of the grinding tool.

Figure 13:
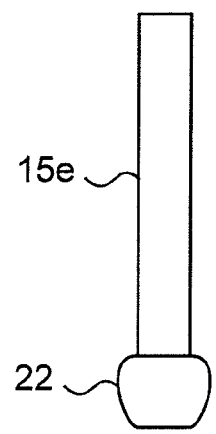
FIG. 13 is a diagram illustrating a front view of a pear-type grinding tool according to a fifth embodiment.

Alternatively, as illustrated in FIG. 13, a grinding tool 15e having a processing section 22 with a pear-shaped tip can perform grinding only from one axial direction.

The form of the processing surface of the grinding tool 15 greatly influences the state of the grinding surface of the denture after processing. Thus, the grinding by the grinding machine 10 may be performed by two different steps, a rough-girding step and a finish-grinding step. Since the processing state varies every time the different grinding tool 15 is used, it is preferable to perform grinding while measuring the shape of the processing surface of the grinding tool 15 and setting the processing angle and position based on the measured shape before the processing. In addition, at the time of grinding, it is preferable to apply a constant pressure load to the grinding tool 15.

It is preferable that the grinding of the front tooth maxilla lingual surface is performed by bringing down the grinding tool 15 in the labial side.

It is preferable that the grinding of the front tooth lower jaw labial surface is performed by bringing down the grinding tool 15 in the lingual side.

It is preferable that the grinding of the buccal surface of each molar cusp is performed by bringing down the grinding tool 15 in the lingual side.

It is preferable that the grinding of the lingual surface of each molar cusps performed by bringing down the grinding tool 15 buccal side.

The direction of bringing down the grinding tool 15 in the buccal side or the lingual side is determined by the inclination of the amplitude direction of the ultrasonic vibration.

The number of types of grinding tools 15 can be lessened and the angles of the grinding tools 15 can be changed to more efficiently perform grinding.

Grinding portion data is acquired by the above-mentioned method.

EXAMPLES

Using various kinds of grinding tools and methods, artificial tools on a denture were subjected to grinding. Sound generation, cutting time, polishing surface state, maxillomandibular conformity, and maxillomandibular touching state were evaluated.

1. Manual Work

An electric router equipped with a diamond bar was used as a grinding tool.

2. Rotation Cutting by Pear Type Grinding Tool

Figure 14A:
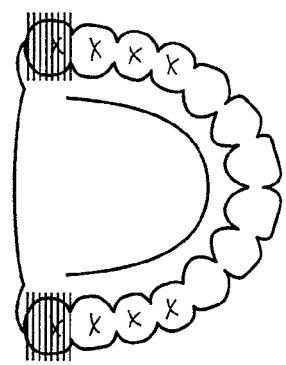
FIGS. 14A and 14B are diagrams each illustrating a sequence of grinding a denture by a grinding tool.

Grinding of the occlusal surface of a denture was performed on the occlusal surface from the right-angled direction using a pear-type rotation cutting tool having a pear-type processing section of 2 mm in diameter. As illustrated in FIG. 14A, a pitch was 300 micrometers from the molar side with a rate of 2 seconds per pitch.

Although a pear-type rotation cutting tool of 1 mm in diameter was also tried, the cutting tool was deformed and was not able to cut.

3. Ultrasonic Polishing by Pear Type Grinding Tool

Grinding of the occlusal surface of a denture was performed on the occlusal surface from the right-angled direction using a pear-type rotation cutting tool having a pear-type processing section of 2 mm in diameter. A pitch was 300 micrometers from the molar side with a rate of 4 seconds per pitch. Although a pear type rotation cutting tool of 1 mm in diameter was also tried, a cutting tool was deformed and was not able to cut. Since the polishing surface having a pitch of 300 micrometers was coarse, the pitch was changed to 100 micrometers, but it took a polishing time of 1 hours or more.

4. Ultrasonic Grinding by Grinding Tool of FIG. 11

Figure 14B:
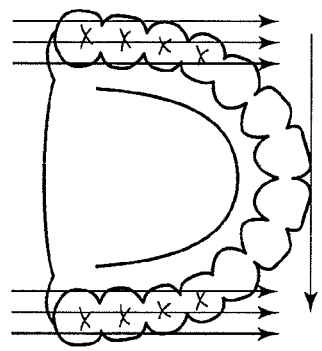

A grinding tool 15c illustrated in FIG. 11 was used. The grinding tool 15c was made of diamond abrasive material and had the tip roundness and the tip both-side end roundness of 0.35 mm in diameter, a tip side corner of 60 degrees, and a tip width of 3.5 mm. As illustrated in FIG. 14B, polishing was performed sequentially from the buccal side of the single jaw to finally the front tooth. The results of each grinding are listed in Table 1.

TABLE 1

| Type of work | Contents of work | Noise | Cutting time | Grinding surface | Maxillo-mandibular conformity | Maxillo-mandibular touching state |
|---|---|---|---|---|---|---|
| 1 | Manual labor | ○ | X 2 hours | ◉ | Δ | X |
| 2 | Rotation cutting by pear-type grinding tool | X | ◉ 10 minutes | Δ | Δ | Δ |
| 3 | Ultrasonic polishing by pear-type grinding tool | ○ | ○ 20 minutes | ○ | Δ | ○ |
| 4 | Ultrasonic polishing by grinding tool of FIG. 11 | ○ | ◉ 13 minutes | ◉ | ◉ | ◉ |

Noise

In work 1, no large sound was generated. In work 2, large motor sound and cutting sound occurred. In work 3, no sound in particular and it was quiet. In work 4, sound of moving denture-holding stand occurred but no other sound and it was quiet.

Cutting Time

In work 1, a lot of time was required because of polishing by hand. In work 2, high cutting force was obtained and polishing time was short. In work 3, polishing time was not so long and occlusal adjustment was possible in clinical treatment. In work 4, polishing time was not so long and occlusal adjustment was possible in clinical treatment.

Grinding Surface

In work 1, since polishing was performed by hand, grinding surface was smooth. In work 2, grinding surface had cutting traces which required polishing. Plaques might be adhered if no polishing was performed. In work 3, beautiful finish was obtained. Substantially no roughness was observed, but some tool marks remained. In work 4, beautiful finish was obtained. Substantially no roughness was observed.

Maxillomandibular Conformity

In work 1, perfect conformity was impossible. In work 2, insufficient conformity was caused by the cutting trace. In work 3, some resistance was caused by the tool mark. In work 4, smooth and beautiful finish was obtained.

Maxillomandibular Touching State

In work 1, only the specific surface had hit. In work 2, insufficient contact occurred due to cutting traces. In work 3, insufficient contact portions occurred due to tool marks. In work 4, sufficient contact was obtained without tool marks and smooth movement was obtained entirely.

What is claimed is:

1. A denture grinding machine, comprising:
   a denture-holding table for holding dentures;
   a grinding tool for grinding the dentures held on the denture-holding table;
   a main body for holding the grinding tool;
   a moving mechanism for causing relative movement between the denture-holding table and the main body; and
   a driving mechanism for relatively driving the main body and the denture-holding table,
   wherein the moving mechanism moves relatively the denture-holding table and the main body in three-dimensional coordinate directions based on grinding portion data,
   wherein the grinding tool performs grinding of the denture occlusal surface from a direction perpendicular to the occlusal surface,
   wherein the grinding portion data uses data prepared by
   (1) a jaw-relation reproduction operation of determining a jaw-relation reproduction condition by obtaining a jaw movement information, and reproducing a jaw state of the patient on an occlusion-state reproducing apparatus in accordance with the jaw-relation reproduction condition,
   (2) a pre-grinding denture production operation of arranging dentures on the occlusion-state reproducing apparatus in accordance with the jaw-relation reproduction condition, and preparing pre-grinding dentures,
   (3) a measurement operation of measuring denture data with reference points comprising three-dimensional image data of an occlusal surface of the dentures and reference points that represent a positional relationship between the jaw-relation reproduction condition and the pre-grinding dentures,
   (4) an occlusion-state reproduction operation of reproducing an occlusion state of the denture data with reference points by using the jaw-relation reproduction condition on a three-dimensional image,
   (5) a grinding data determination operation of determining grinding data of grinding portions under a dynamic condition or set condition from a portion surrounded by an image of upper and lower jaws on the three dimensional image in a reproduced occlusal state, and
   (6) a preparation operation of preparing denture data with reference points having grinding data, where the denture data with reference points is additionally provided with the grinding data.

2. The denture grinding machine according to claim 1, wherein
   the grinding tool has a grinding surface on a tip thereof inclined with respect to an axis line, where the grinding surface faces at least one of an occlusion facet on a moving side, an occlusion facet of a working side, and an occlusion facet at forward moving, of the artificial tooth that forms the denture.

3. The denture grinding machine according to claim 1, wherein the drive mechanism is a vibratory device with an ultrasonic vibrator.

4. The denture grinding machine according to claim 2, wherein the drive mechanism is a vibratory device with an ultrasonic vibrator.

5. The denture grinding machine according to claim 1, wherein the jaw movement information is obtained from a movement of a patient.

6. The denture grinding machine according to claim 1, wherein the jaw movement information is obtained from a movement of an articulator.

7. A denture grinding method, comprising:
   holding dentures using a denture-holding table;
   grinding the dentures held on the denture-holding table using a grinding tool;
   holding the grinding tool with a main body;
   causing relative movement between the denture-holding table and the main body using a moving mechanism;

relatively driving the main body and the denture-holding table using a driving mechanism; and preparing grinding portion data;

wherein the moving mechanism moves relatively the denture-holding table and the main body in three-dimensional coordinate directions based on the grinding portion data, wherein the grinding tool performs grinding of the denture occlusal surface from a direction perpendicular to the occlusal surface, wherein said preparing the grinding portion data includes (1) a jaw-relation reproduction operation of determining a jaw-relation reproduction condition by obtaining a jaw movement information, and reproducing a jaw state of the patient on an occlusion-state reproducing apparatus in accordance with the jaw-relation reproduction condition, (2) a pre-grinding denture production operation of arranging dentures on the occlusion-state reproducing apparatus in accordance with the jaw-relation reproduction condition, and preparing pre-grinding dentures, (3) a measurement operation of measuring denture data with reference points comprising three-dimensional image data of an occlusal surface of the dentures and reference points that represent a positional relationship between the jaw-relation reproduction condition and the pre-grinding dentures, (4) an occlusion-state reproduction operation of reproducing an occlusion state of the denture data with reference points by using the jaw-relation reproduction condition on a three-dimensional image, (5) a grinding data determination operation of determining grinding data of grinding portions under a dynamic condition or set condition from a portion surrounded by an image of upper and lower jaws on the three dimensional image in a reproduced occlusal state, and (6) a preparation operation of preparing denture data with reference points having grinding data, where the denture data with reference points is additionally provided with the grinding data.

8. The denture grinding method of claim 7, wherein the grinding tool has a grinding surface on a tip thereof inclined with respect to an axis line, where the grinding surface faces at least one of an occlusion facet on a moving side, an occlusion facet of a working side, and an occlusion facet at forward moving, of the artificial tooth that forms the denture.

9. The denture grinding method of claim 8, wherein the drive mechanism is a vibratory device with an ultrasonic vibrator.

10. The denture grinding method of claim 7, wherein the drive mechanism is a vibratory device with an ultrasonic vibrator.

11. The denture grinding method of claim 7, wherein the jaw movement information is obtained from a movement of a patient.

12. The denture grinding method of claim 7, wherein the jaw movement information is obtained from a movement of an articulator.

* * * * *